(12) United States Patent  (10) Patent No.: US 7,763,156 B2
Jean et al.  (45) Date of Patent: Jul. 27, 2010

(54) APPARATUS FOR ELECTROPHORESIS

(76) Inventors: Tzu-Chao Jean, No. 10, Lane 423, Gongguan Road, Beitou District, Taipei (TW) 112; Wu-Yang Ma, No. 15-6, Fengxi Street, Xiaogang District, Kaohsiung (TW) 812

( * ) Notice: Subject to any disclaimer, the term of this patent is extended or adjusted under 35 U.S.C. 154(b) by 646 days.

(21) Appl. No.: 11/681,439

(22) Filed: Mar. 2, 2007

(65) Prior Publication Data

US 2007/0205108 A1   Sep. 6, 2007

(30) Foreign Application Priority Data

Mar. 3, 2006  (TW) ............................... 95107330 A

(51) Int. Cl.
*G01N 27/453* (2006.01)

(52) U.S. Cl. ...................................... 204/618; 204/616
(58) Field of Classification Search ......... 204/606–621, 204/456–467
See application file for complete search history.

(56) References Cited

U.S. PATENT DOCUMENTS 6,110,340 A * 8/2000 Lau et al. ..................... 204/467
6,162,342 A   12/2000 Perez et al.
7,276,143 B2 * 10/2007 Chen .......................... 204/618

FOREIGN PATENT DOCUMENTS

TW           277920        10/2005

* cited by examiner

*Primary Examiner*—Alex Noguerola
(74) *Attorney, Agent, or Firm*—Pai Patent & Trademark Law Firm; Chao-Chang David Pai

(57) ABSTRACT

The present invention provides a gel-casting module, a main electrophoresis assembly, a casting stand for the main electrophoresis assembly and an electrophoresis tank.

14 Claims, 10 Drawing Sheets

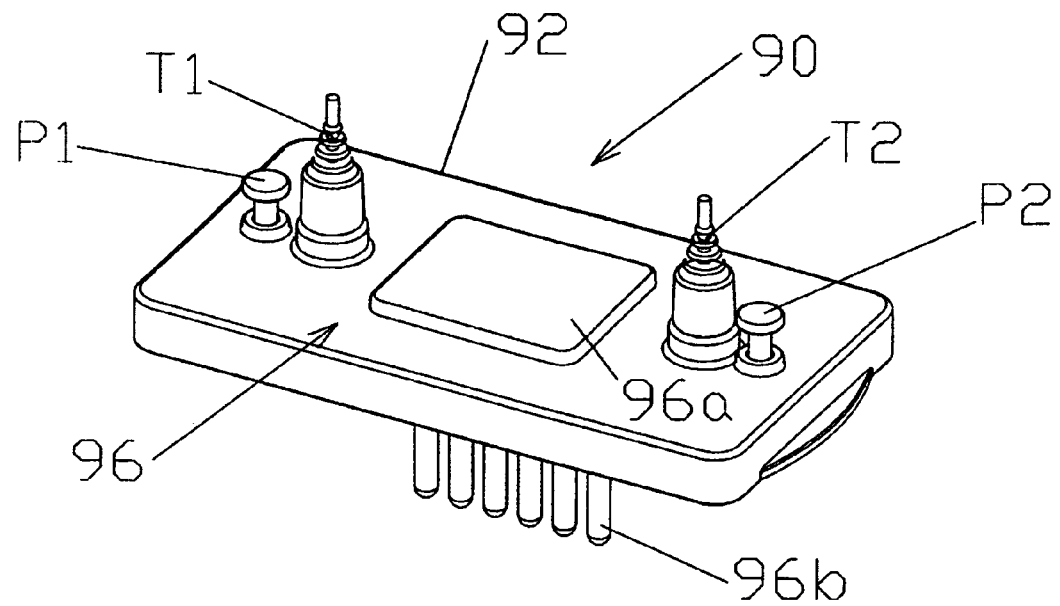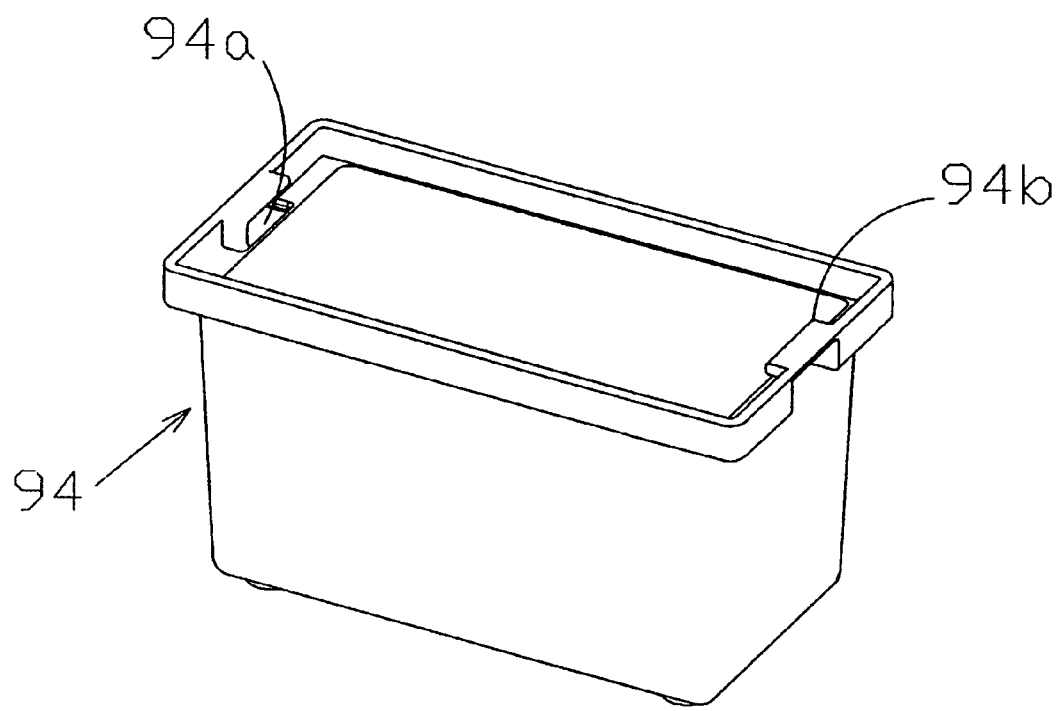
Fig. 9

APPARATUS FOR ELECTROPHORESIS

RELATED APPLICATIONS

The present application is based on, and claims priority from, Taiwan Application Serial Number 95107330, filed Mar. 3, 2006, the disclosure of which is hereby incorporated by reference herein in its entirety.

BACKGROUND

1. Field of Invention

The present invention relates to an apparatus for electrophoresis. More particularly, the present invention relates to a gel-casting module, a main electrophoresis assembly, a casting stand, and an electrophoresis tank.

2. Description of Related Art

Electrophoresis is a kind of analytic technology widely applied in molecular biology and related fields. By using electrophoresis equipment, some charged particles such as DNA, RNA, or proteins can be separated from small ionic molecules or even from a whole cell.

When electrophoresis is carried out by gel substrates, it is called gel electrophoresis. Generally speaking, electrophoresis equipment should provide a gel-casting module for casting gels and a retaining frame for settling the gel-casting module while applying electrophoresis. The gel-casting module usually comprises a pair of plates parallel arranged and a pair of spacers. By clipped by the retaining frame, the pair of plates is spaced by the pair of spacers, and the left and right sides of the pair of plates are closed so that a specific volume of a gel space is formed therebetween.

To assure that there is no leak while casting a gel, It not only needs to insure that the left and right sides of the gel space are both sealed, but should also make sure that the bottom of the gel space is enclosed. Therefore, some electrophoresis equipments even provide a casting stand to seal the bottom of the gel space by placing the gel-casting module, clipped by the retaining frame as described above, on the casting stand.

The gel-casting modules in the art adopt a pair of flat striped spacer to separated a pair of parallel plates to form a gel space as disclosed in U.S. Pat. No. 6,162,342 and Taiwan Utility Model Registration No. TW 277920. The retaining frames and the casting stands in the art are also disclosed in these previous skills.

A retaining frame disclosed in the U.S. patent above comprises a pair of deformable retaining members and a pair of rotatable lever-operated cam. Each retaining members have grooves on the left and right sides to receive the two gel-casting modules. By rotating the lever-operated cam, the retaining members are distorted so that both left and right sides of the gel-casting module are clamped. Next, the clamped gel-casting modules are placed on a casting stand. Finally, the opening at the bottom edges of the gel-casting module is sealed by a clam and a gasket arranged at the top and the bottom of the casting stand respectively.

A retaining frame disclosed in the TW patent above is cooperated with a casting stand. There is a concave arranged on the retaining frame for a gel-casting module to lean upon. In addition, a cover that can be overturned and overlapped on the concave is arranged below the concave of the retaining frame. Clasps for fastening or releasing the cover are placed on both shoulders of the retaining frame.

However, the flat striped spacer disclosed in the art is not convenient for use. Moreover, because the retaining frame adopts too many components, the structure of it is so complex that results in the high cost.

In addition, the closure between the bottom of the gel-casting module and the gasket is maintained by the resilient of the gasket in the art. Thus, the gel might leak and the analysis result will be affected due to elastic fatigue. At that time, the gasket needs to be changed which causes extra loading for maintaining.

Furthermore, according to electrophoresis process in the art, bubbles will aggregate on the gel-casting module that results in obstructing observation. However, no solution is provided in the art.

SUMMARY

For the forgoing reasons, there is a need for solving problems mentioned above.

It is therefore an objective of the present invention to provide a gel-casting module, a main electrophoresis assembly, a casting stand and an electrophoresis tank.

According to one embodiment of the present invention, the main electrophoresis assembly comprises a bracket, at least one gel-casting module, and a plurality of clamps. The bracket includes a plurality of electrical terminals connecting to electrodes, and at least one bubble exhaustion structure. The gel-casting module comprises at least two plates and a pair of spacers. The plurality of clamps is used for detachably securing the gel-casting module on the bracket. The gel-casting module and the bracket can be integrated with each other via the clipping force of the clamps. In addition, a first space is formed by parallel spacing the at least two plates by the pair of the spacers and a second space is formed between each of the clamps and the bracket. While processing electrophoresis, bubbles produced in the reaction are guided and gathered in the second space by the bubble exhaustion structure.

According to one embodiment of the present invention, the bubble exhaustion structure is a notch arranged at the bottom of the bracket. The surface of the notch shows a v-shaped cross section in both vertical and horizontal directions simultaneously. Moreover, the "V" has a tilt angle from 0 degree to 30 degrees.

According to one embodiment of the present invention, the bracket has a plurality of tabs connecting the upper portion of walls of the bracket. The tabs stop bubbles and are used for observing.

It is another objective of the present invention to provide a casting stand which comprises a station, an engaging component, and a sealing component. The engaging component arranged on the station is used for securing the main electrophoresis assembly. The sealing component arranged on the station comprises at least one closure member and resilient member to seal the bottom of the at least one gel-casting module of the main electrophoresis assembly.

It is another objective of the present invention to provide an electrophoresis tank which comprises a chamber and a lid. The chamber has an opening wherein a main electrophoresis assembly comprising at least one gel-casting module can be detachably secured in the interior. The lid comprises a plurality of electrical terminals connecting to electrodes and a heat dissipation apparatus. When the opening of the chamber is covered by the lid, the heat dissipation apparatus is located around the at least one gel-casting module of the main electrophoresis assembly.

According to one embodiment of the present invention, a plurality of mounting members located on the peripheral of the opening, the mounting members engaged with a plurality of blockers to fix a main electrophoresis assembly inside the electrophoresis tank The structures of the gel-casting module, the main electrophoresis assembly, the casting stand, and the electrophoresis tank are used cooperatively or individually depending on the situation.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 9 is an exploded view of the electrophoresis tank in accordance with an embodiment of the present invention;

DESCRIPTION OF THE PREFERRED EMBODIMENTS

Figure 1B:
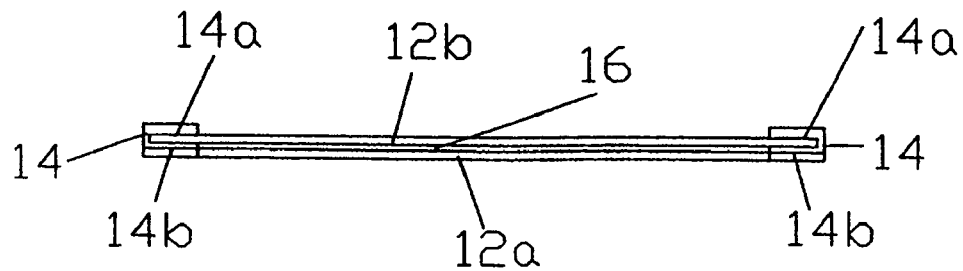
FIG. 1B is a top view of the gel-casting module of FIG. 1A after assembling, in accordance with an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

Figure 1A:
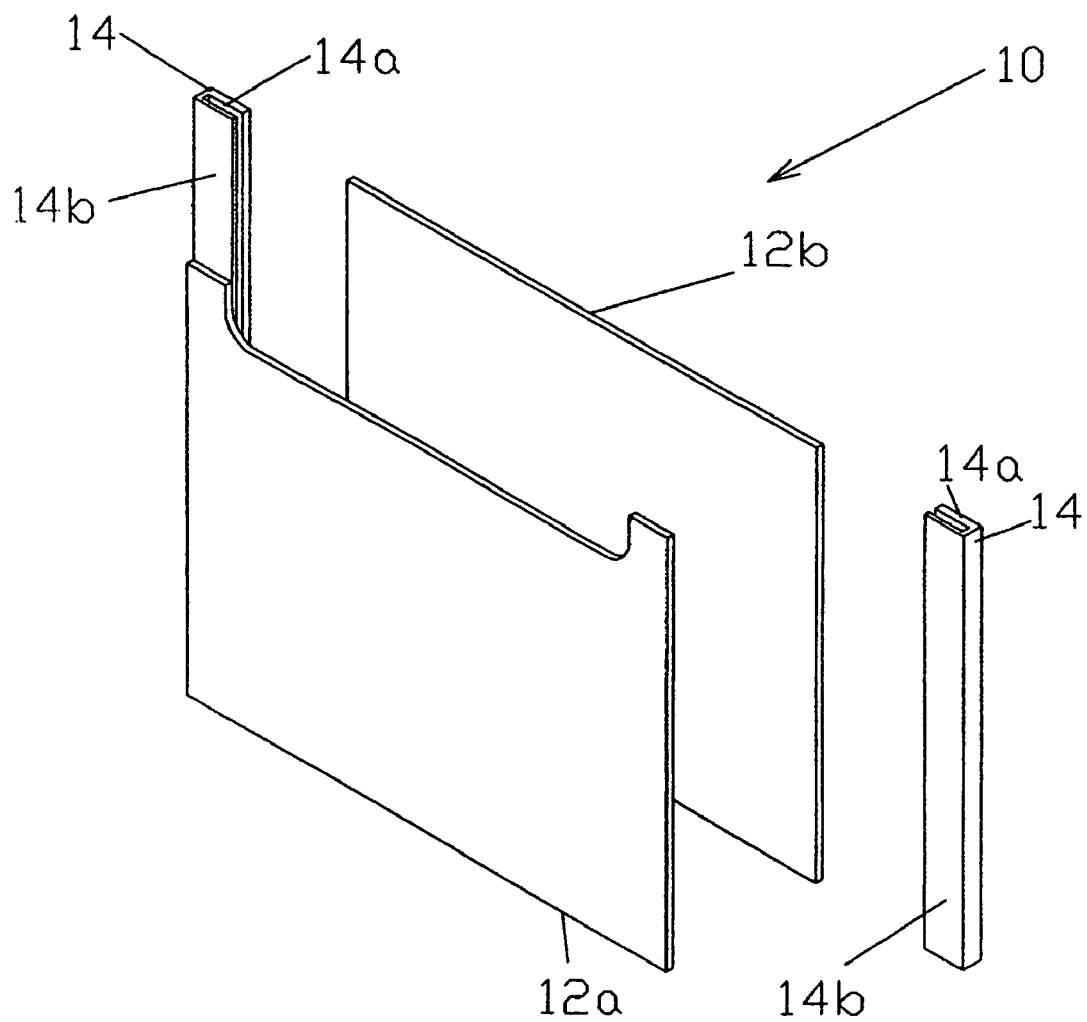
FIG. 1A is an exploded view of a gel-casting module in accordance with an embodiment of the present invention.

FIG. 1A illustrates an exploded view of a gel-casting module 10 in accordance with an embodiment of the present invention. The gel-casting module 10 comprises a pair of plates 12a and 12b, and a pair of spacers 14. According to one feature of the present invention, there is a channel 14a arranged within each spacer 14. The material of plates 12a and 12b are transparent material, such as glass or acrylic. In addition, the top edge of plate 12a is a little bit concave for observing sample more easily in the later processing.

FIG. 1B illustrates a top view of the gel-casting module 10 of FIG. 1A after assembling. The plates 12b is inserted into channel 14a and the plate 12a is overlapped on the outer surface 14b of the spacer 14 to form a gel space 16. To maintaining the gel space 16, a retaining frame is needed for clamping the gel-casting module 10 (depicted later).

Figure 2B:
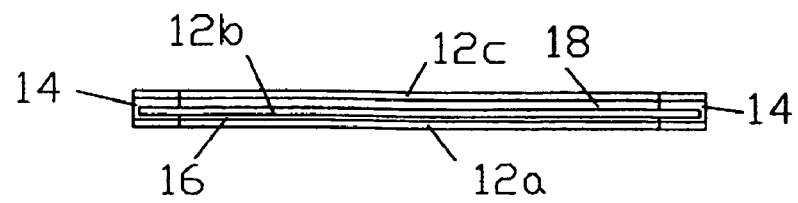
FIG. 2B is a top view of the gel-casting module of FIG. 2A after assembling, in accordance with an embodiment of the present invention.
Figure 2A:
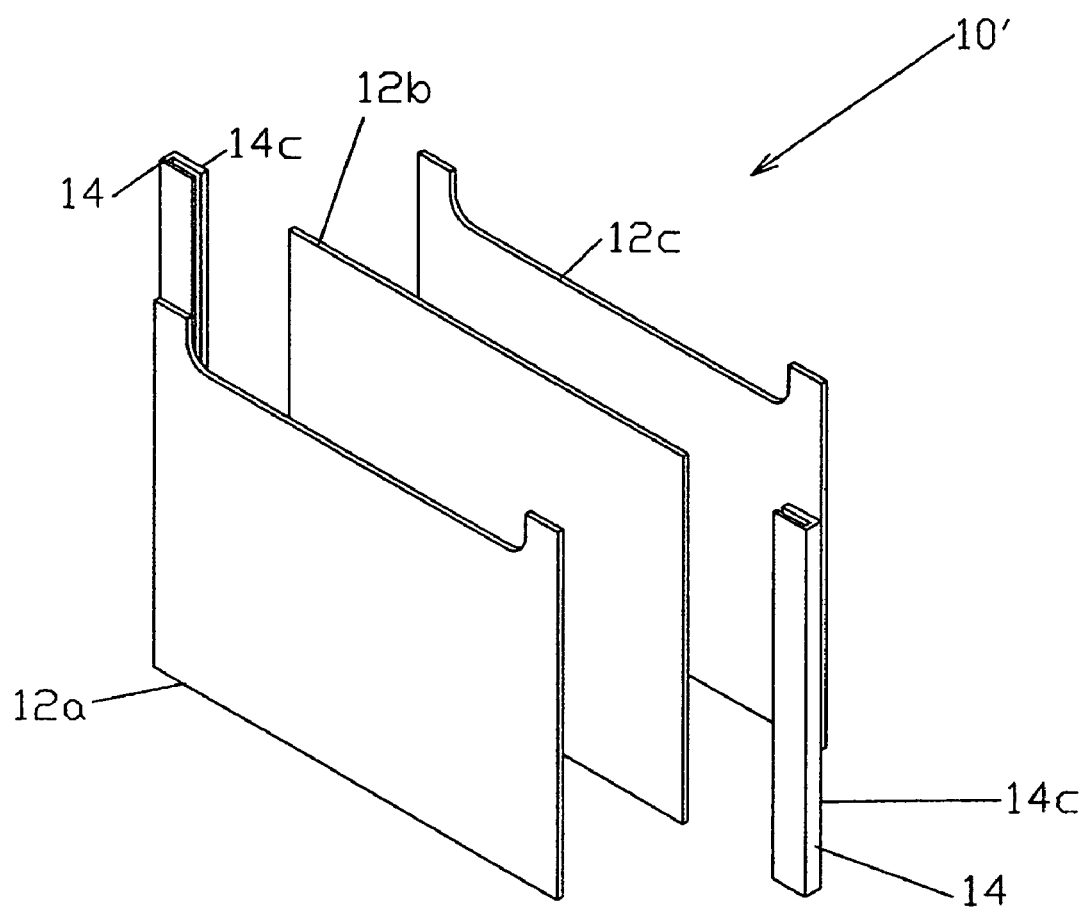
FIG. 2A is an exploded view of a gel-casting module in accordance with an embodiment of the present invention.

FIG. 2A illustrates one situation of the embodiment of FIG. 1 while using three plates, wherein the plate 12c of the gel-casting module 10' is overlapped on the other outer surface 14c of the spacer 14. Therefore, not only the original gel space 16 but also an additional gel space 18 is formed as shown in FIG. 2B.

For the pair of single channel spacers provided by the present invention, there are two casting spaces formed at most. However, for the flat spacers in the prior art, two pairs of spacers are needed to form two identical casting spaces. This is one of advantages of the channel-typed spacer of the present invention. Another advantage of the channel-typed spacer is that the channel itself is good for holding the plates.

Figure 3B:
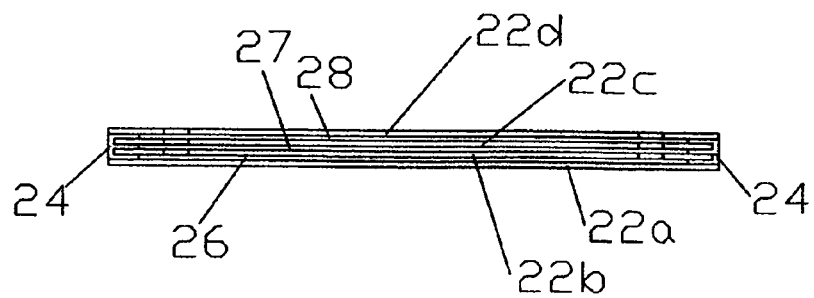
FIG. 3B is a top view of the gel-casting module of FIG. 3A after assembling, in accordance with an embodiment of the present invention.
Figure 3A:
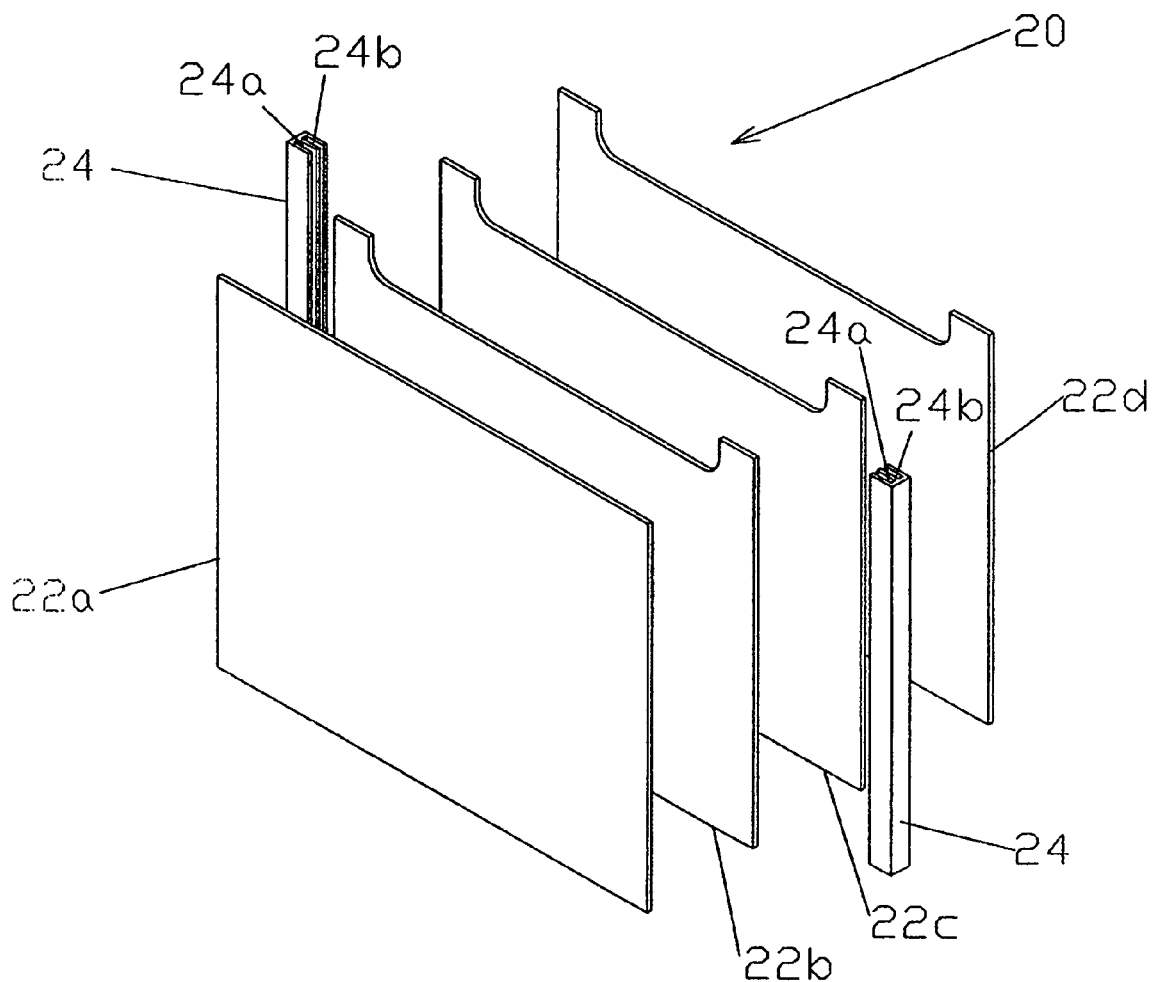
FIG. 3A is an exploded view of a gel-casting module in accordance with an embodiment of the present invention.

If more than two casting spaces are desired, it just needs to increase the numbers of the channels within the spacers as shown in FIG. 3. In FIG. 3A, the gel-casting module 20 comprises a pair of spacers 24, and there are two channels 24a and 24b arranged in each spacer 24. Thus, three gel spaces 26, 27 and 28 are partitioned by four plates 22a-22d, as illustrated in FIG. 3B.

The volume of the casting spaces above is determined by the thickness of the walls of the channels of the spacers. If the walls of the channels are with the same thickness, the volume of the casting spaces will be the same. In contrast, if the thickness of the walls of the channels are varied, the volume of the casting spaces will be changed, which is determined by designer's requirement.

Moreover, while the gel-casting module is used for casting gel, a retaining frame is needed for clamping. Although any kinds of retaining frame in the art could be used herein, a better clamping effect will be provided if main electrophoresis assembly provided by the present invention is used.

Figure 4B:
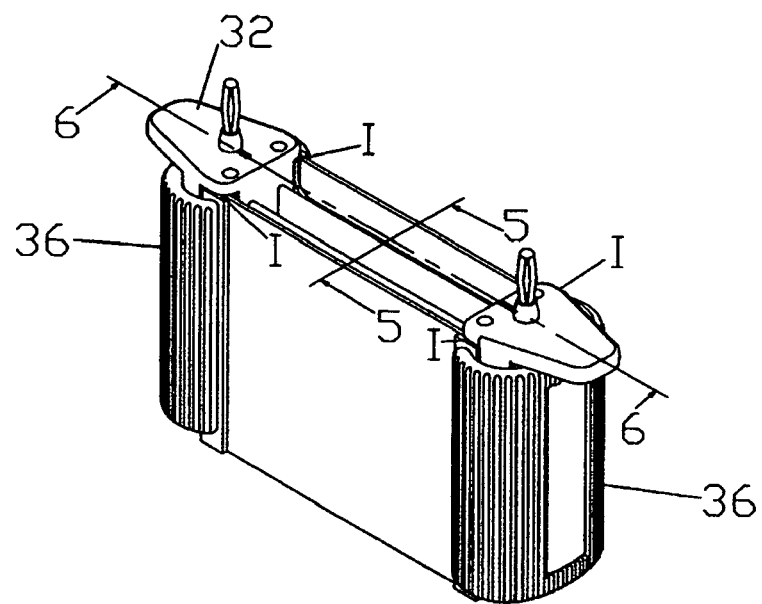
FIG. 4B is an elevation view of the main electrophoresis assembly of FIG. 4A after assembling, in accordance with an embodiment of the present invention.
Figure 4A:
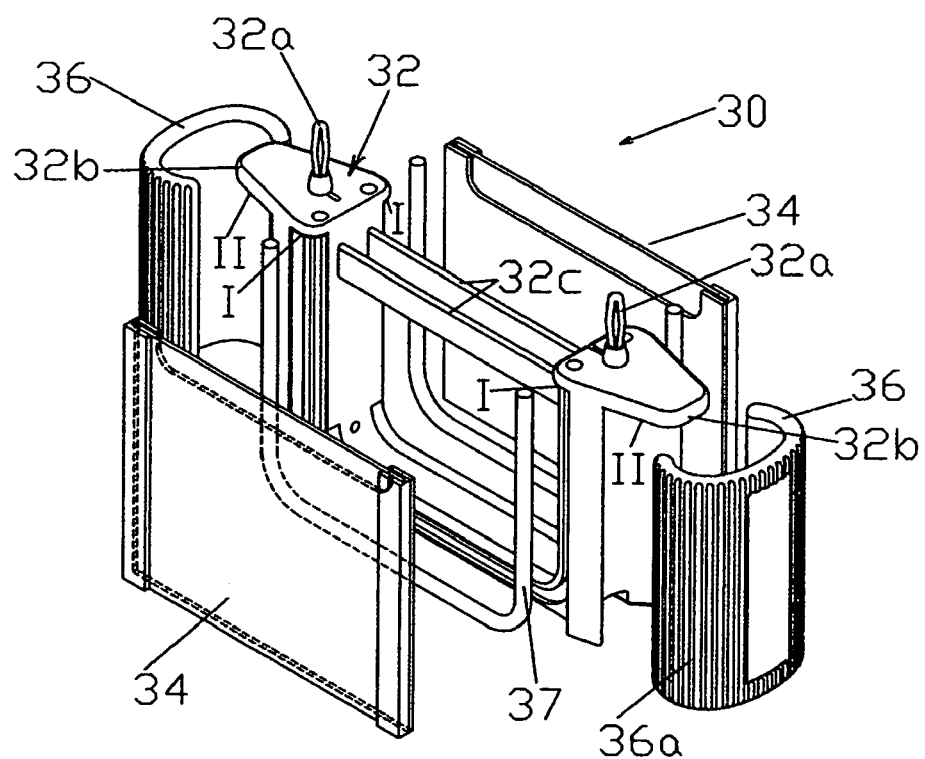
FIG. 4A is an exploded view of a main electrophoresis assembly in accordance with an embodiment of the present invention.

FIG. 4A illustrates an exploded view of a main electrophoresis assembly in accordance with an embodiment of the present invention. The main electrophoresis assembly 30 comprises a bracket 32, two sets of gel-casting modules 34, and a pair of clamps 36. The main component of bracket 32 is a U-shaped structure that both ends are extended horizontally to form a pair of ears 32b to form a first blocker I and a second blocker II (the function thereof will be described later). A pair of electrical terminals 32a is arranged on the ears 32b, which connects to the electrodes inside the bracket (not illustrated).

In addition, for observing more conveniently, although it is not necessary, a pair of light color tab 32c is arranged on the bracket 32.

Even though the two sets of the gel-casting module 34 are illustrated as the gel-casting module shown in FIG. 1, it is not limited to that. One set of gel-casting module or any kinds of gel-casting module in the art are also applicable (as long as the size is fit). In addition, a strip 37 is also arranged between the gel-casting module 34 and the bracket 32 as a buffer.

The clamp 36 is made of any kind of flexibility material such as metal, engineering plastics, etc. The appearance of the clamp 36 is broadly C-shaped, but it is not limited to this. The grooves 36a are formed on the surface of the clamp 36 for holding.

FIG. 4B is an elevation view of the main electrophoresis assembly of FIG. 4A after assembling. The C-shaped structure of the clamp 36 provides enough clamping force to clip the gel-casting module 34 on the bracket 32, and a part of top edge of each set of the gel-casting module 34 is against the first block I of the bracket 32. Compared with the complex lever-operated cam or the clasps in the art, the C-shaped structure of the clamp 36 is much simpler and provides more efficient clamping force.

Figure 4C:
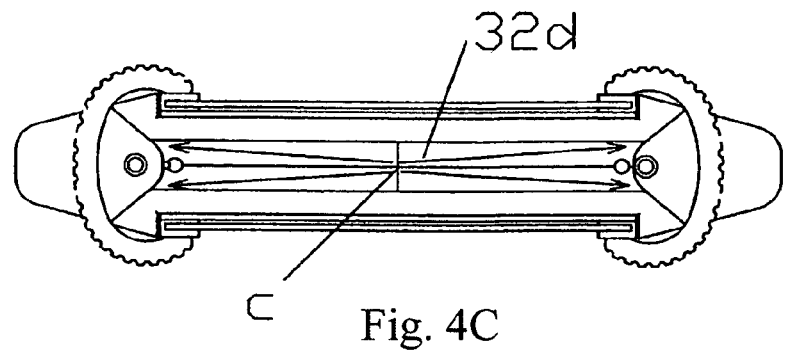
FIG. 4C is a bottom view of bracket in accordance with an embodiment of the present invention.
Figure 5:
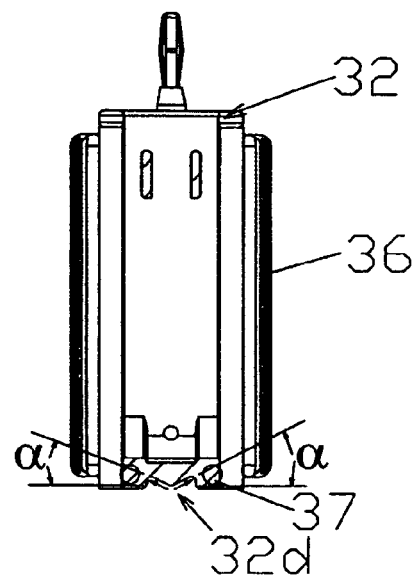
FIG. 5 is a cross-section view of the directions 5-5 in FIG. 4B in accordance with an embodiment of the present invention.
Figure 6:
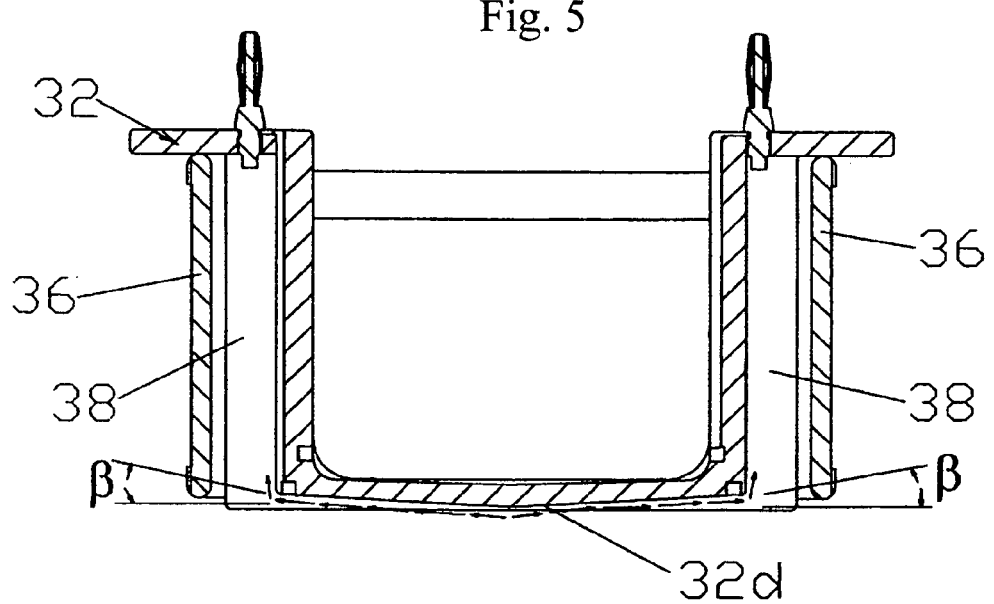
FIG. 6 a cross-section view in the directions 6-6 of FIG. 4B in accordance with an embodiment of the present invention.

According to one of the features of the present invention, a bubble exhaustion structure is arranged at the bottom of the bracket 32. Referring to FIG. 4C, which is a bottom view of bracket 32, the surface of the bubble exhaustion structure is a notch 32d which is ridged instead of flat. The highest point of the ridge is located on the approximate center C of the surface. The arrows in the Figs. Indicate the routes that bubbles might be guided. In order to represent the tilt conditions of the surface of the notch 32d more clearly, two cross-sections are provided in two directions 5-5 (horizontal) and 6-6 (vertical). The results are shown in FIG. 5, and FIG. 6 respectively (For simplifying, the gel-casting module 34 is not illustrated in all of these cross-section figures.) According to FIG. 5 and FIG. 6, the surface of the notch 32d is shown as a V-shaped cross-section with a tilt angle $\alpha$ in the horizontal side, and with a tilt angle $\beta$ in the vertical side respectively. The value of tilt angles $\alpha$ and $\beta$ are, for example, from 5° to 30°.

The arrangement of the tilt angles $\alpha$ and $\beta$ in the vertical and horizontal side is one of unique designs of the present invention. Bubbles produced during the electrophoresis process will be removed along the route shown by arrows in FIG. 5 and FIG. 6, and are further gathered in the gap 38 formed between the bracket 32 and the clamp 36. Thus, no more bubble will aggregate on the gel-casting module that might obstruct observation as what happens in the art.

Up to FIG. 4, only the left and right sides of the gel-casting module 10 of the main electrophoresis assembly 30 are enclosed but the bottom side is not. With respect to this, in the art, one method not so strict is to enclose the bottom side by taping and then a gel is cast. Although this method is not excluded, it is not reliable and not allowable for steady arrangement. Therefore, a preferred method is that the main electrophoresis assembly 30 is positioned in the casting stand 70 as shown in FIG. 7A and then casting a gel is performed.

Figure 7:
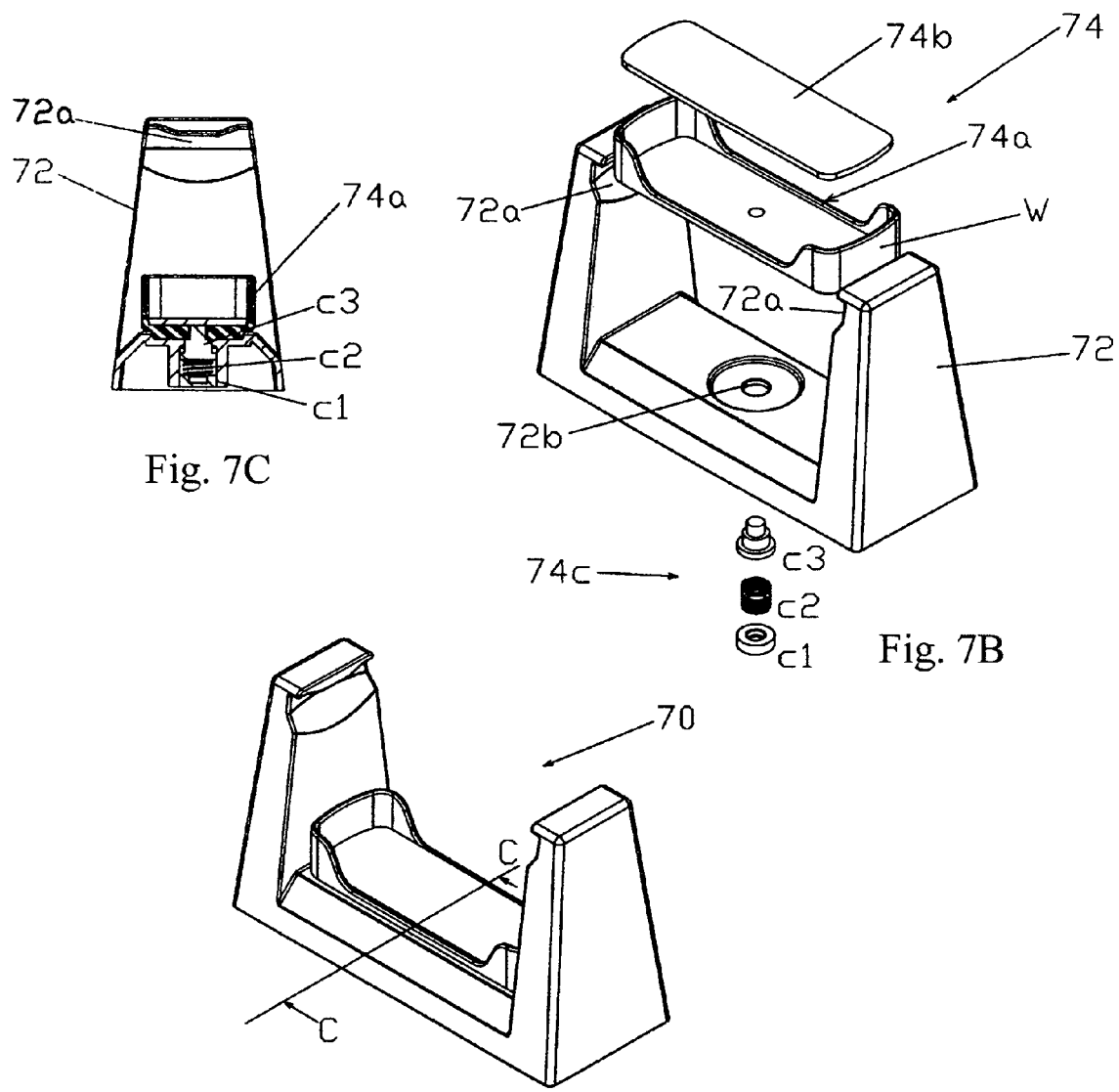
FIG. 7A is an elevation view of the casting stand, in accordance with an embodiment of the present invention.
FIG. 7B is an exploded view of the casting stand in accordance with an embodiment of the present invention.
FIG. 7C is a cross-section view in the directions C-C of FIG. 7A in accordance with an embodiment of the present invention.

Referring to FIG. 7B, the casting stand 70 comprises a station 72 and a supporting base 74 as an enclosing part. The station 72 is U-shaped profile wherein a pair of concaves 72a is arranged inside of the top of both arms of the U-shaped as an engaging component. The supporting base 74 further comprises a tray 74a, a gasket 74b, and an elasticity adjustment 74c. The elasticity adjustment 74c comprises a set screw C1, a spiral spring C2, and a lever C3. While assembling, referring to FIG. 7C, a cross-section view in CC direction of FIG. 7A, the bottom of the tray 74a is integrated with lever C3, and the underneath of lever C3 is connected with the spiral spring C2, and the underneath of the spiral spring C2 is secured by set screw C1. Thus, the tray 74a is biased by the upper elasticity from the spiral spring C2 and the elasticity can be adjusted by rotating the set screw C1.

Figure 8:
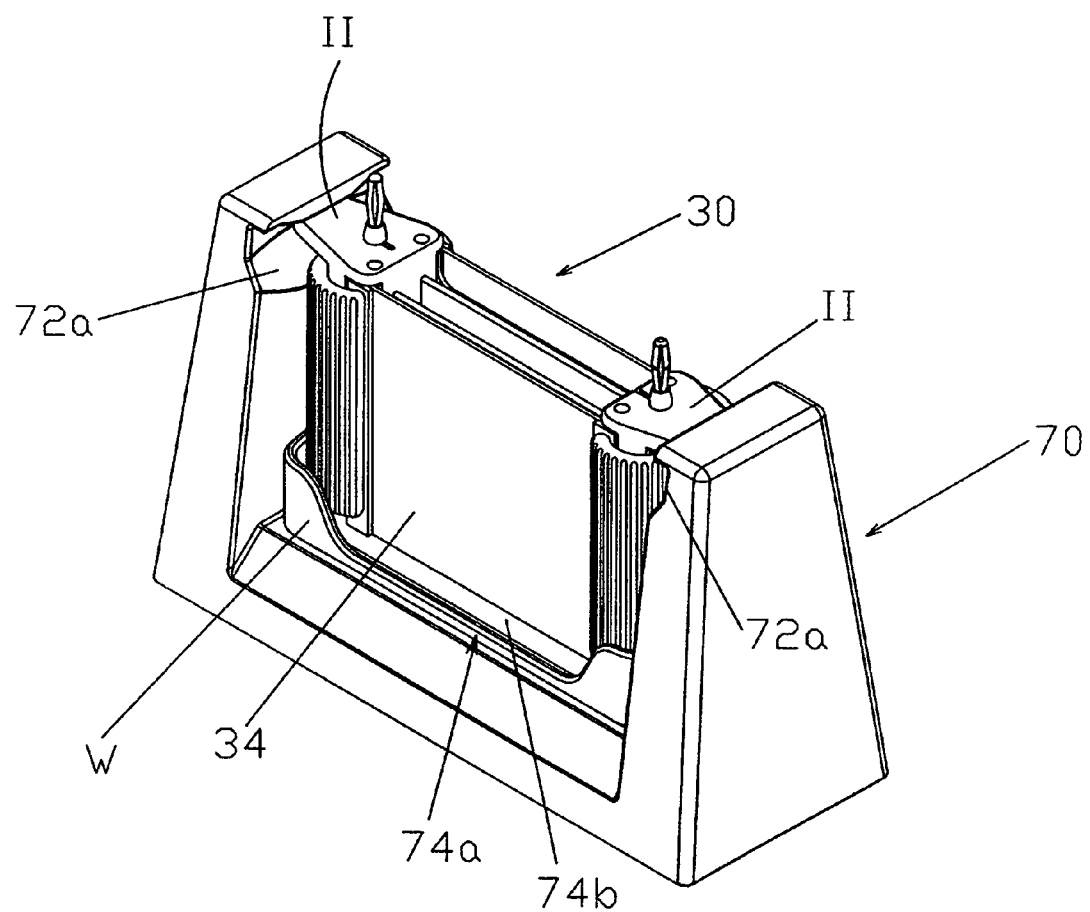
FIG. 8 is a situation of the main electrophoresis assembly held by casting stand in accordance with an embodiment of the present invention.

FIG. 8 illustrates a situation of the main electrophoresis assembly 30 held by casting stand 70. A pair of the second blockers 11 of the main electrophoresis assembly 30 is accommodated by a pair of concaves 72a provided by the casting stand 70 herein, and the lateral wall W prevents the bottom of the main electrophoresis assembly 30 from sliding. The tray 74a is pushed upward by elasticity from the spiral spring C2 so that the second blocker II is against the concave 72a. As a result, the bottom of the gel-casting module 34 is tightly closed by the gasket 74b on the tray 74a through the elasticity from the spiral spring C2. In the embodiment of the present invention, the bottom of the gel-casting module 34 is enclosed by the elasticity from the spiral spring C2 instead of the elasticity from the gasket itself. Hence, no more elasticity fatigue happens.

The main electrophoresis assembly 30 is illustrated as an example in FIG. 8 herein. In practice, the casting stand 70 can be used for any kind of the main electrophoresis assemblies in the art as long as those main electrophoresis assemblies comprise ears similar to the second blocker II and are with suitable size.

The main electrophoresis assembly 30 in FIG. 8 is applicable for pouring gel fluid and then the main electrophoresis assembly 30 is removed from the casting stand 70 after pouring gel fluid. Next, electrophoresis is performed and this needs to place the main electrophoresis into an electrophoresis tank 90. FIG. 9 illustrates an exploded view of the electrophoresis tank 90 wherein the electrophoresis tank 90 comprises a lid 92 and a chamber 94. According to one feature of the present invention, a heat dissipation apparatus 96 is arranged on the lid 92 wherein the heat dissipation apparatus 96 consists of a heat dissipating member 96a and a heat conducting member 96b. The material of the heat dissipating member 96a can be any kind of material that dissipates heat easily wherein metals are usually preferred, such as copper or aluminum. A plurality of heat tubes is used for the heat conducting member 96b, and these tubes extend downward from the heat dissipating member 96a and pass through the lid 92. A pair of electrical terminals T1 and T2, and a pair of press pins P1 and P2 helping to take off the cap are arranged on the cap. The chamber 94 only has one single-surface opening and a pair of mounting trenches 94a and 94b is arranged on the edge of the opening.

Figure 10A:
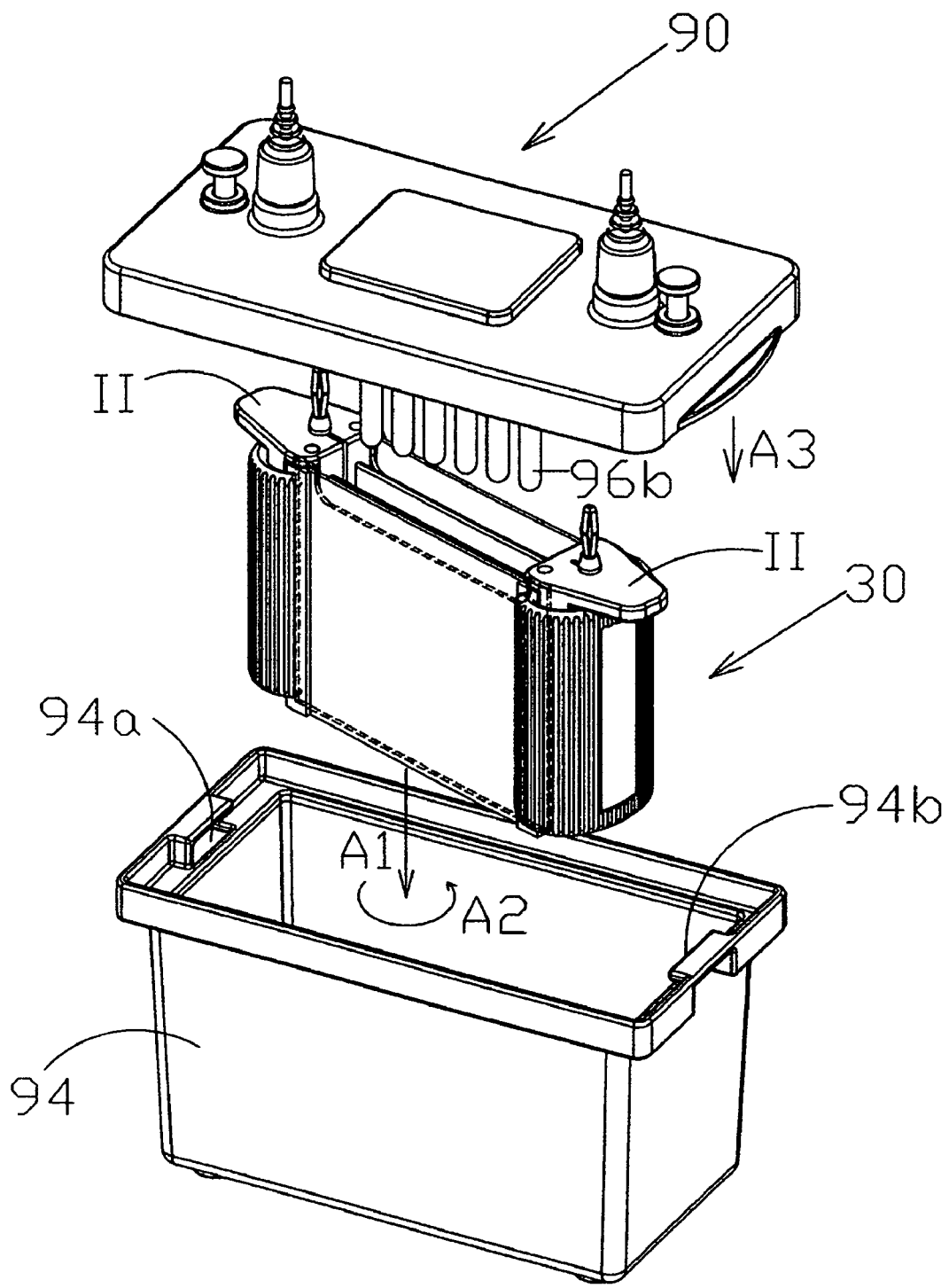
FIG. 10A illustrates a process of placing the main electrophoresis assembly into the electrophoresis tank in accordance with an embodiment of the present invention.

FIG. 10 illustrates a process of placing the main electrophoresis assembly 30 into the electrophoresis tank 90. According to the direction indicated by an arrow A1 as shown in FIG. 10, the main electrophoresis assembly 30 is placed downward into the electrophoresis tank 90 first till the second blocker II is level with the mounting trenches 94a and 94b. Next, the main electrophoresis assembly 30 is rotated in the direction indicated by the arrow A2 as shown in FIG. 10 so that the second blockers II are mounted in the mounting trenches 94a and 94b and the main electrophoresis assembly 30 is hanged in the chamber 94. Finally, the lid 92 is capped on the chamber 94 in the direction shown as arrow A3 in the figure. It is notable that the heat conducting member 96b needs to be extended into the main electrophoresis assembly 30.

Figure 10B:
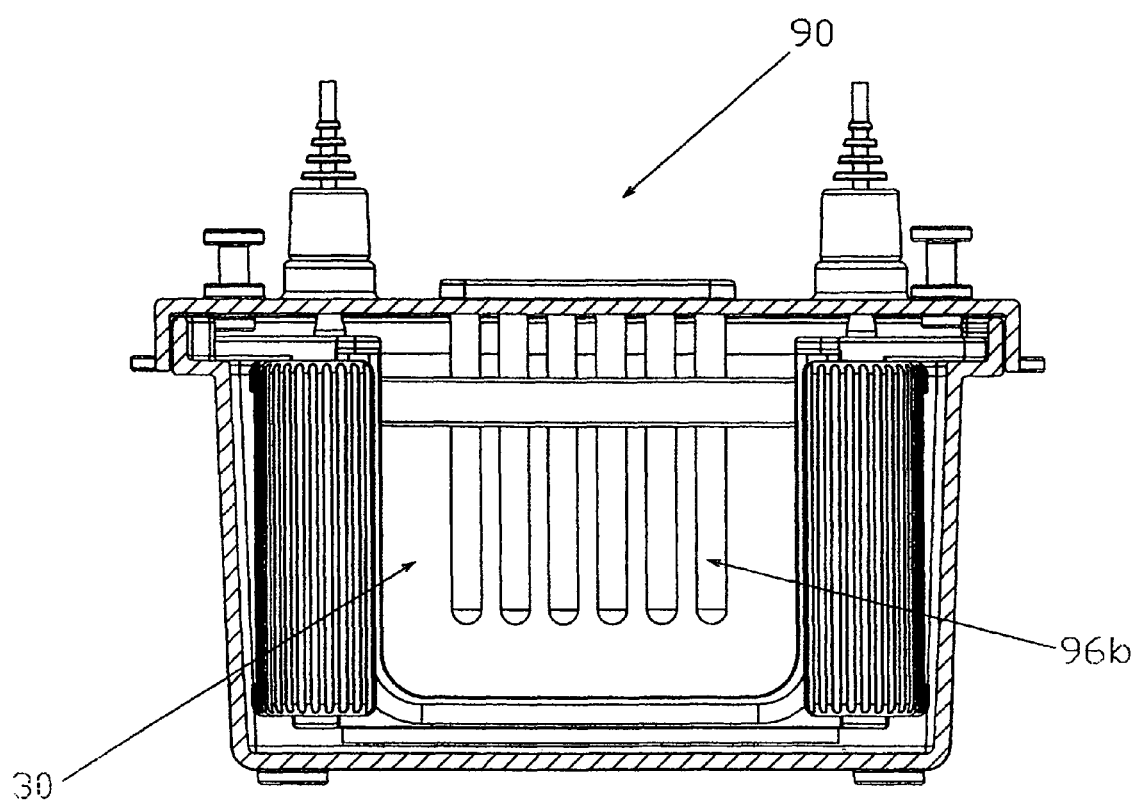
FIG. 10B is a vertically assembling cross-section view of placing the main electrophoresis assembly 30 into the electrophoresis tank 90 in accordance with an embodiment of the present invention.

FIG. 10B illustrates a vertically assembling cross-section view of placing the main electrophoresis assembly 30 into the electrophoresis tank 90. Since the heat conducting member 96b is extended into the main electrophoresis assembly 30, the heat produced by the electrophoresis can be conducted efficiently.

The main electrophoresis assembly 30 is illustrated as an example in FIG. 10 herein. In practice, the electrophoresis tank 90 can be used for any kind of the main electrophoresis assemblies in the art as long as those main electrophoresis assemblies comprises ears similar to the second blocker II that are with suitable size.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A main electrophoresis assembly, comprising:
    a bracket, comprising:
        a plurality of electrical terminal for connecting electrodes; and
        a bubble exhaustion structure located on a bottom of the bracket; and
    at least one gel-casting module, comprising:
        at least two plates, wherein at least one of the plates is transparent; and
        at least one pair of spacers, each spacer having one pair of channels, wherein each plate has been inserted into a channel in one of said spacers and also into a channel of another of said spacers so that a first space is located between plates in the channels of one pair of spacers;
    a plurality of clamps fixing the gel-casting module into the bracket, a second space located between the bracket and the clamps, wherein the second space is led to the bubble exhaustion structure.

2. The main electrophoresis assembly as claim 1, wherein the bubble exhaustion structure is a notch.

3. The main electrophoresis assembly as claim 2, wherein a shape of cross sections of a horizontal directions and vertical direction of the notch is "V".

4. The main electrophoresis assembly as claim 3, wherein the "V" has a tilt angle from 0 degree to 30 degrees.

5. The main electrophoresis assembly as claim 1, wherein the bracket has a plurality of tabs connecting the upper portion of walls of the bracket, the tabs stop bubbles and are used for observing.

6. The main electrophoresis assembly as claim 5, wherein the bracket has a plurality of first blockers connecting the upper potion of the walls.

7. The main electrophoresis assembly as claim 6, wherein the bracket has a plurality of second blockers on the outside surface of the wall.

8. The main electrophoresis assembly as claim 7, further comprising a casting stand, comprising:
    a station;
    an engaging component located on the station; and
    a sealing component for sealing the bottom of the gel-casting module, the sealing component located on a bottom of the station, the sealing component comprising:
        a closure member; and
        a resilient member located under the closure member.

9. The main electrophoresis assembly as claim 8, wherein the engaging component comprises a plurality of concaves for engaging the second blockers.

10. The main electrophoresis assembly as claim 6, wherein a shape of the clamps is "C".

11. The main electrophoresis assembly as claim 8, wherein the sealing component further comprises an elasticity adjustment a elasticity of the resilient member.

12. The main electrophoresis assembly as claim 11, wherein the elasticity adjustment has a set screw and a spiral spring.

13. The main electrophoresis assembly as claim 6, wherein the clamps have grooves on the outside surface.

14. The main electrophoresis assembly as claim 1, further comprising buffer located between the gel-casting module and the bracket.

* * * * *